United States Patent
Bakker et al.

(10) Patent No.: US 11,872,165 B2
(45) Date of Patent: *Jan. 16, 2024

(54) AERODYNAMIC RAIL COVERS

(71) Applicant: KONINKLIJKE PHILIPS N.V., Eindhoven (NL)

(72) Inventors: Cornelis Pieter Bakker, Waalre (NL); Nikolai Chikovskii, Eindhoven (NL); Maikel Van Eekelen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/086,723

(22) Filed: Dec. 22, 2022

(65) Prior Publication Data
US 2023/0130118 A1 Apr. 27, 2023

Related U.S. Application Data

(63) Continuation of application No. 16/955,853, filed as application No. PCT/EP2018/084425 on Dec. 12, 2018, now Pat. No. 11,576,831.

(30) Foreign Application Priority Data

Dec. 20, 2017 (EP) ..................... 17208895

(51) Int. Cl.
| | | |
|---|---|---|
| *A61G 13/10* | (2006.01) |
| *A61B 6/00* | (2006.01) |
| *A61G 12/00* | (2006.01) |

(52) U.S. Cl.
CPC .......... *A61G 13/108* (2013.01); *A61B 6/4423* (2013.01); *A61B 6/4464* (2013.01); *A61G 12/004* (2013.01); *A61G 2210/50* (2013.01)

(58) Field of Classification Search
CPC ................ A61G 13/108; A61G 12/004; A61G 2210/50; A61B 6/4464; A61B 6/4423;
(Continued)

(56) References Cited

U.S. PATENT DOCUMENTS

| | | |
|---|---|---|
| 4,946,484 A | 8/1990 | Monson et al. |
| 8,523,644 B2 | 9/2013 | Melles |

(Continued)

FOREIGN PATENT DOCUMENTS

| | | |
|---|---|---|
| CN | 107355970 A | 11/2017 |
| GB | 2216251 A | 4/1989 |
| WO | 2016116389 A1 | 7/2016 |

OTHER PUBLICATIONS

PCT/EP2018/084425 WO & ISR, Feb. 22, 2019, 13 Page Document.

*Primary Examiner* — Irakli Kiknadze

(57) ABSTRACT

An aerodynamic rail cover for an operating room with laminar airflow is provided. The rail cover comprises a rail cover component configured to be movably attached to a support rail of a ceiling mounted support arrangement of a medical imaging system. The rail cover component comprises a base element and an air guiding surface element connected to the base element. The base element is configured to be attached to a portion of the support rail of the ceiling mounted support arrangement. The air guiding surface element forms an air guide to be mounted at least temporarily to cover a portion of the support rail of the ceiling mounted support arrangement. The air guiding surface element comprises two surface parts that extend from starting edges on opposite sides of the base element to a common trailing edge.

15 Claims, 13 Drawing Sheets

(58) Field of Classification Search
CPC ..... A61B 6/4441; A61B 6/4488; A61B 6/037;
A61B 6/032; A61B 6/035; A61B 6/04;
A61B 6/40; A61B 6/4435; A61B 6/4447;
A61B 5/055; F24F 13/078; F24F 7/06
USPC ........................................................ 454/292
See application file for complete search history.

(56) References Cited

U.S. PATENT DOCUMENTS

| | | | |
|---|---|---|---|
| 11,576,831 B2 * | 2/2023 | Bakker | ................ A61G 13/108 |
| 2008/0101546 A1 | 5/2008 | Delmas | |
| 2015/0097564 A1 | 4/2015 | Maciejewski | |
| 2017/0101779 A1 | 4/2017 | Schreiber | |
| 2017/0325763 A1 | 11/2017 | Hoernig et al. | |
| 2018/0008219 A1 * | 1/2018 | Opheij | ................ A61G 13/108 |
| 2018/0368794 A1 | 12/2018 | Krug | |

* cited by examiner

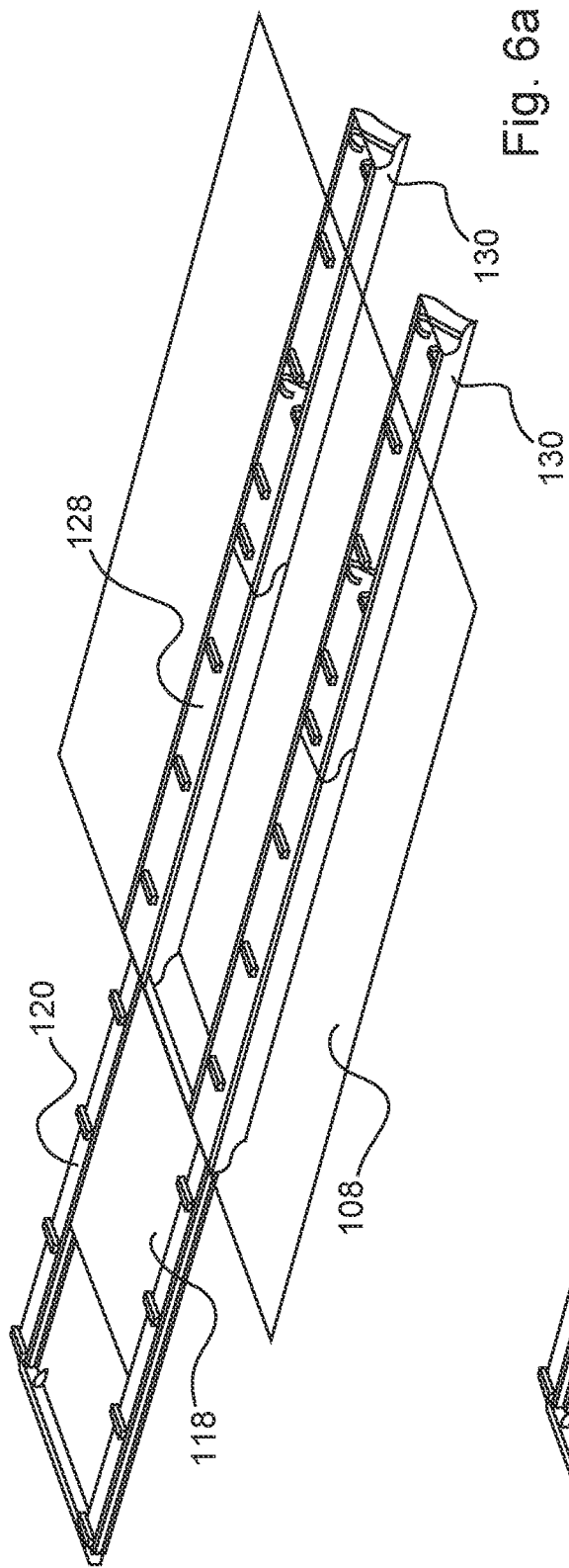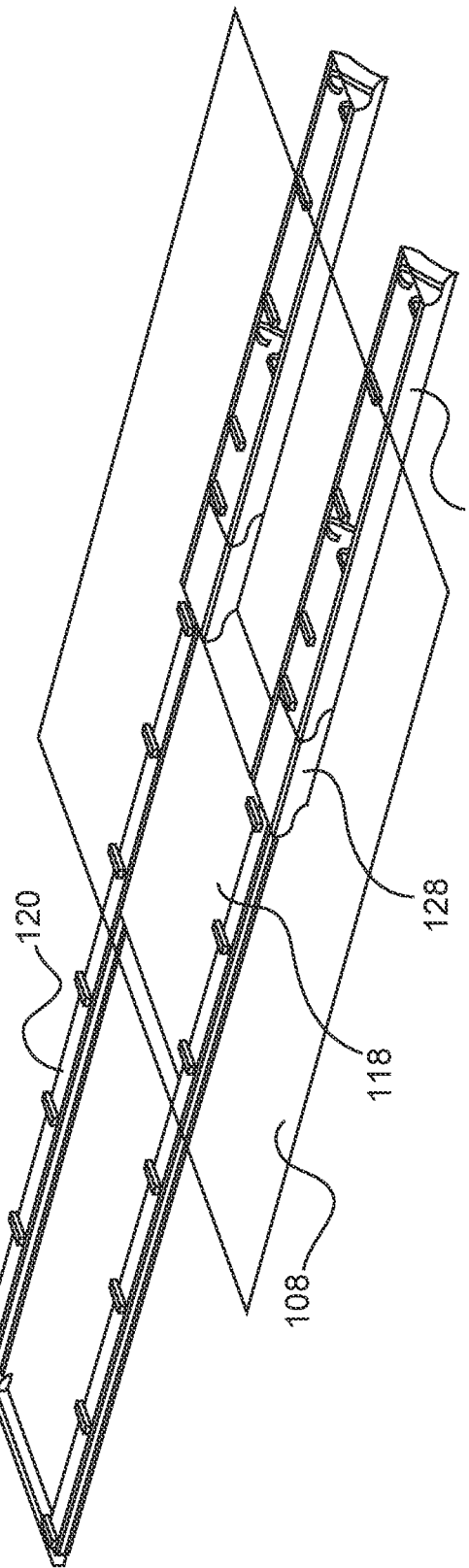

AERODYNAMIC RAIL COVERS

CROSS-REFERENCE TO RELATED APPLICATIONS

This application is a continuation application of U.S. application Ser. No. 16/955,853, filed on Jun. 19, 2020, now issued as U.S. Pat. No. 11,576,831, which is a U.S. National Phase application under 35 U.S.C. § 371 of International Application No. PCT/EP2018/084425 filed Dec. 12, 2018, which claims the benefit of European Patent Application No. 17208895.7, filed on Dec. 20, 2017. These applications are hereby incorporated by reference herein.

FIELD OF THE INVENTION

The present invention relates to an aerodynamic rail cover for an operating room with laminar airflow, to a laminar airflow system for an operating room with a medical imaging system, to a medical imaging system for an operating room with laminar airflow, to an operating room arrangement with a laminar airflow and to a method for providing a laminar airflow for an operating room.

BACKGROUND OF THE INVENTION

For operations or other medical interventions, e.g. in a hospital, air supply requirements may exist, in particular with regards to the patient area in an operating room, which zone is also referred to as the operating zone. Temperature, air speed, relative humidity and also limited values for different grades of air purity in the sterile operating zone exist. In order to prevent contaminated environmental air entering the operating zone to prevent exposure of the patient's body to airborne contaminants while he/she is being operated, for example during surgical interventions and also during medical imaging procedures, treated air, e.g. filtered, cleaned or sterilized air, may be supplied to the operating zone. As an example, laminar air flow (LAF) units provide an air downflow from the ceiling, e.g. from the ceiling downwards towards a patient table, to cover the zone of the operating table and some of the adjacent surrounding zone. However, the air downflow may be affected by medical equipment suspended from the ceiling, such as an X-ray imaging system. As an example, WO 2016/116389 A1 describes an air supply for providing a laminar downflow to an operating zone, wherein the carriage also provides an air downflow. Nevertheless, support structures in the ceiling area may still impair the laminar air downflow.

SUMMARY OF THE INVENTION

There may thus be a need to provide measures to improve the provision of a laminar airflow in an operating zone.

The object of the present invention is solved by the subject-matter of the independent claims; further embodiments are incorporated in the dependent claims. It should be noted that the following described aspects of the invention apply also for the aerodynamic rail cover for an operating room with laminar airflow, for the laminar airflow system for an operating room with a medical imaging system, for the medical imaging system for an operating room with laminar airflow, for the operating room arrangement with a laminar airflow and for the method for providing a laminar airflow for an operating room.

According to the present invention, an aerodynamic rail cover for an operating room with laminar airflow is provided. The rail cover comprises at least one cover component that comprises a base element and an air guiding surface element connected to the base element. The base element is configured to be attached to a portion of a support rail of a ceiling mounted support arrangement of a medical imaging system. The air guiding surface element forms an air guide to be mounted at least temporarily to cover a portion of the support rail and comprises two surface parts that are extending from starting edges on opposite sides of the base element to a common trailing edge. Further, the rail cover component is configured to be movably attached to the support rail of the ceiling mounted support arrangement of a medical imaging system.

This provides a possibility to improve the laminar airflow field and to increase the size of the spatially continuously provided laminar airflow.

The air guiding surface element comprises the two surface parts. The surface parts each extend from the starting edges to the trailing edge. The surface parts are thus forming the air guide.

In an example, the rail cover component is configured to be movably connected to the support rail to be movable along the support rail.

In an example, the term "base element" and "an air guiding surface element" relate to separate constructive components that are mounted to each other. In another example, the terms relate to integral parts of a bi-functional component.

In an example, a single aerodynamic rail cover is provided, for example when a support rail arrangement only comprises a single support rail. Or when only one or a pair of rails is affecting a flow field of a laminar airflow.

In a preferred example, a pair of rail covers, or a rail cover pair, is provided, for example when a support rail arrangement comprises a pair, i.e. two support rails. Or when two rails out of two or more rails is affecting a flow field of a laminar airflow.

As an example, it is provided a pair of trail covers that are configured with the same or similar cross section, i.e. the same or similar aerodynamic effective surface or profile.

As another example, it is provided a pair of trail covers that are configured with different sections, i.e. different aerodynamic effective surfaces or profiles.

According to an example, the rail cover component is configured to be slidably attached to the support rail of the ceiling mounted support arrangement of a medical imaging system.

According to an example, a sliding guiderail arrangement is provided with cover support guiderails to be arranged along each longitudinal side of the support rail. The rail cover component is slidably suspending from the cover support guiderails.

In another option, the rail cover component is slidably suspending from the support rail.

According to an example, at least two cover segments are provided. At least one of the at least one cover segments is arrangeable on the rail in a temporarily displaceable manner to provide an adjustable rail cover segment. One of the at least two cover segments is at least partly insertable into one of the other at least two cover segments. The at least two cover segments are forming a telescopic cover component.

In an example, an area of the support rail between the two outer cover segments remains uncovered.

According to an example, three cover segments are provided. A first outer segment, a middle segment and a second outer segment are provided. The two outer segments are provided with a wider cross-section such that they can be moved over the middle segment.

In an example, the two outer segments each have half the length of the middle segment.

In an example, the two outer segments and the middle segment are movably attachable to a guiding rail.

In an example, the rail cover component is an adaptable rail cover component comprising at least one telescopic cover segment with a plurality of telescopic cover elements. Preferably, one end of the adaptable cover component is configured to be fixed, whereas the other end is configured to be displaceable providing a rail cover component with adaptable length.

In an example, the rail cover component is an adaptable rail cover component that comprises at least one telescopic cover segment with a plurality of telescopic cover elements.

In addition, or alternatively, the rail cover component is an adaptable rail cover component that comprises at least one bellows cover segment. For example, the bellows cover segment is provided as a harmonic folding rail cover. The length of the cover can be varied by compression or expansion of a flexible bag-like structure, i.e. like a bellow arrangement.

In an example, two cover segments are provided, and one of the two cover segments is fixedly mountable to the support rail to provide a fixed rail cover segment, and the other of the two cover segments is arrangeable on the rail in a temporarily displaceable manner to provide an adjustable rail cover segment.

The displaceable cover segment may be provided as movable or as a cover that changes the outer shape, such as telescopic segments. To move or displace the cover segment(s) allows to make use of the guide rails that are otherwise covered by the cover segments. However, when some parts of the rail segments are not used, the movable covers provide to restore the laminar flow.

Preferably, the adjustable rail cover segment is provided as a movable cover segment. The movable cover segment is at least partly insertable into the fixed rail cover segment, or the fixed rail cover segment is at least partly insertable into the movable cover segment. The two cover segments are forming a telescopic cover component.

The telescopic cover component can also be referred to as an adaptable telescopic rail cover component.

The aerodynamic rail cover is also referred to as ARC.

In an example, the ARC is split in a fixed, hollow piece and a movable piece with a slightly smaller cross-section so that it will slide into the hollow/fixed piece when it is propelled by the X-ray systems longitudinal carriage.

The configuration of this example provides that the laminar airflow is undisturbed (by the ceiling rails) when the X-ray system is parked. Further, the rail cover allows the X-ray carriage to travel the full length of the rail. Still further, the fixed, hollow part of the aerodynamic cover extends beyond the end of the rail and has a length, sufficient to store the travel length of the movable rail cover.

In another example, a multiple stage telescopic rail cover is provided. Multiple segments, similar shaped, are sliding along the rail which segments slide into each other when propelled by the X-ray systems longitudinal carriage. In an example, the two surface parts each provide an essentially equal guiding length between the starting edges and the trailing edge.

According to an example, a coupling is provided for connecting the movable rail cover component to a carriage of an imaging system, which carriage moves along the support rail. The rail cover is configured to cover the support rail. The coupling is provided as a magnetic coupling that is dis-connectable if the carriage moves outside the covering range of the rail cover.

When the carriage is moved, and abuts a cover segment, the cover segment can simply be moved by forward pushing. When moving in the opposite direction, for example back after a target positon has been reached, the cover segment is also pulled back by the magnetic connector. If the cover segment has reached its final destination, and the carriage is moved further, the magnetic connection disconnects.

It is noted that the magnetic coupling is provided as an option. Also, other detachable connecting mechanisms are provided.

In an example, two cover components are provided for covering portions of each rail of a pair of support rails.

In an example, two cover segments are provided, and one of the two cover segments is fixedly mountable to the support rail to provide a fixed rail cover segment, and the other of the two cover segments is arrangeable on the rail in a temporarily displaceable manner to provide an adjustable rail cover segment. In an option, the adjustable rail cover segment is provided as a movable cover segment. The movable cover segment is at least partly insertable into the fixed rail cover segment, or the fixed rail cover segment is at least partly insertable into the movable cover segment i.e. the movable cover segment is wider such that it can be moved across the fixed cover segment. The two cover segments are forming a telescopic cover component.

According to an example, the starting edges are configured to be arranged next to border regions of a laminar airflow plenum such that an intermediate region between two laminar airflow fields is bridged by the air guiding surface element in order to provide a re-established laminar airflow of the two laminar airflow fields downstream the trailing edge.

In an example, the intermediate region is a region that does not actively contribute to the laminar flow of the laminar airflow fields. For example, the intermediate region is a blocked region that does not provide a laminar airflow in a plane of the laminar airflow plenum field.

In an example, the cover component has a downward protruding dimension in a range of minimum 10 cm and maximum 50 cm, for example 25 cm.

For example, a height of 21 cm for the height of the rail cover is provided.

In another example, the protruding dimension has a maximum of 20 cm. In other words, the rail cover segment has a maximum height of approximately 20 cm.

According to an example, a width of the rail cover segment is defined by the distance between the starting edges, and a height of the rail cover segment is defined by a distance from a plane formed by the starting edges to the common trailing edge. In an example, the width is equal or larger than the height.

In an option, the two surface parts, in their starting portions, each extend from the starting edges in an essentially perpendicular direction to a plane of a ceiling surface. In a further option, additionally or alternatively, the two surface parts, in their trailing edge portions, merge with an acute angle. In a still further option, additionally or alternatively, the two surface parts, in their middle portions, run in an angle wider than the acute angle at the trailing edge, but also narrower that at the starting edges.

It is noted that the shape of the two surface parts with the three options is provided as an additional or alternative option to the width-height ratio.

In an example, the polluted air is entering the LAF area from outside. In this case, the rail cover is installed on the rails in the form of small segments positioned in the border region of the LAF area, where rails are crossing the actual edge of the plenums. This way the covers are re-establishing the airflow in the border region, thus creating an airflow curtain, which isolates the sterile area from the contaminated.

The small segment would be propelled by the ceiling carriage of the X-ray system along the longitudinal rail. This would require the ceiling rail to be elongated by the length of this rail-cover segment in order to maintain the same maximum travel of the X-ray system or alternatively to sacrifice some of its range.

In an example, two cover components are provided for covering portions of each rail of a pair of support rails.

According to the present invention, also a laminar airflow system for an operating room with a medical imaging system is provided. The airflow system comprises at least one laminar airflow outlet configured to provide at least one laminar airflow plenum. The at least one laminar airflow outlet is configured to provide an airflow towards a patient table. A support rail of a ceiling mounted support arrangement of a medical imaging system is arrangeable downstream the laminar airflow outlet or adjacent to the laminar airflow plenum. At least one rail cover for covering at least one part of the support rail. The rail cover is provided as an aerodynamic rail cover according to one of the examples above.

According to an example, the support rail reaches across the outer boundaries of the laminar airflow outlet. The aerodynamic rail cover comprises at least two segments from which at least one is provided as an outer movable segment. The at least one outer movable segment is arrangeable in an area of the outer boundaries of the laminar airflow outlet.

According to an example, the aerodynamic rail cover comprises at least three segments. In addition to the at least one two outer movable segment, at least one forms a middle segment. Further, the at least one outer movable segment is provided with a wider cross section than the middle segment such that the at least one outer movable segment can be moved over the middle movable segment.

According to the present invention, also a medical imaging system for an operating room with laminar airflow is provided. The imaging system comprises an image acquisition arrangement with a source and a detector, a ceiling mounted support arrangement with at least one support rail and a carriage movable along at least a part of the support rail, and at least one rail cover for covering at least one part of the support rail. At least one of the source and detector is movably supported by the carriage. At least a part of the at least one support rail is arrangeable downstream a laminar airflow outlet or adjacent to a laminar airflow plenum provided by the laminar airflow outlet. The rail cover is provided as an aerodynamic rail cover according to one of the examples above.

According to the present invention, also an operating room arrangement with a laminar airflow is provided. The arrangement comprises at least a ceiling region, a laminar airflow system, and a medical imaging system. The laminar airflow system comprises at least one laminar airflow outlet configured to provide at least one laminar airflow plenum. At least one laminar airflow outlet is configured to provide an airflow towards a patient table. The medical imaging system comprises an image acquisition arrangement with a source and a detector, and a support arrangement with at least one support rail mounted in the ceiling region and a carriage movable along at least a part of the support rail. At least one of the source and detector is movably supported by the carriage. Further, at least a part of the at least one support rail is arranged downstream the laminar airflow outlet. At least one rail cover for covering at least one part of the support rail is provided. The rail cover is provided as an aerodynamic rail cover according to one of the examples above.

According to the present invention, also a method for providing a laminar airflow for an operating room is provided. The method comprises the following steps:

a) Providing a first plenum of laminar airflow and a second plenum of laminar airflow. The first and second plenum are separated from each other by a laminar-flow-free region.

b) Guiding a border portion of the first laminar airflow along a first surface part of an air guiding surface, and guiding a border portion of the second laminar airflow along a second surface part of the air guiding surface. The first and second surface parts are extending from starting edges close to the first and second plenum, respectively, to a common trailing edge, wherein the first surface part and the second surface part and the training edge are forming an air guide covering a portion of the laminar-flow-free region. The rail cover component is configured to be movably attached to the support rail of the ceiling mounted support arrangement of a medical imaging system.

According to an aspect, a cover is provided to be placed on components, for example rails, that are arranged within a field of laminar airflow. The cover has two lateral surfaces that meet in a common edge to guide two lateral laminar airflows to form a common laminar airflow. The guiding surfaces thus repair or generate a common field of laminar airflow. The cover is movable along the rails in order to ensure an adaptive cover that still allows movement of equipment along the rails for positioning purposes.

In an example, the two lateral surfaces form a wedge-like cover that provides smooth transition portions in its surface orientations in order to provide guiding to adjacent laminar airflows. The surfaces that are exposed to the adjacent laminar flow have a similar, e.g. parallel orientation to make the laminar flow passing along the surface. The direction changes without abrupt changes but with gentle changes, e.g. by tangential transition portions. The airflow will follow the contour and is thus guided. As the guidance takes place on both sides of the cover, two air flows are directed towards the common trailing edge where the two airflows are combined to one common airflow. As a result, the airflow field no longer has a separation or disturbance caused by the rail. The drawing in of contaminated air from the surrounding into the laminar flow is prevented or at least minimized. Without the cover, a zone of underpressure would be caused in the area of the rails which underpressure would lead to drawing in (contaminated) air from the surrounding.

The rail cover avoids the underpressure by constantly leading the airflow streams on both sides towards each other. Instead of an abrupt zone with lower pressure, the two airflows are distributed in a smooth and continuous manner to form a common laminar airflow field.

These and other aspects of the present invention will become apparent from and be elucidated referring to the embodiments described hereinafter.

BRIEF DESCRIPTION OF THE DRAWINGS

Exemplary embodiments of the invention will be described in the following referring to the following drawings:

FIGS. 6*a* and 6*b* show a rail arrangement with rail covers resulting in an adaptable coverage of the laminar airflow with the aerodynamic rail covers. FIG. 6*a* shows a carriage for an X-ray imaging system in a first position, and FIG. 6*b* shows the carriage in a second position with displaced cover segments.

DETAILED DESCRIPTION OF EMBODIMENTS

Figure 1A:
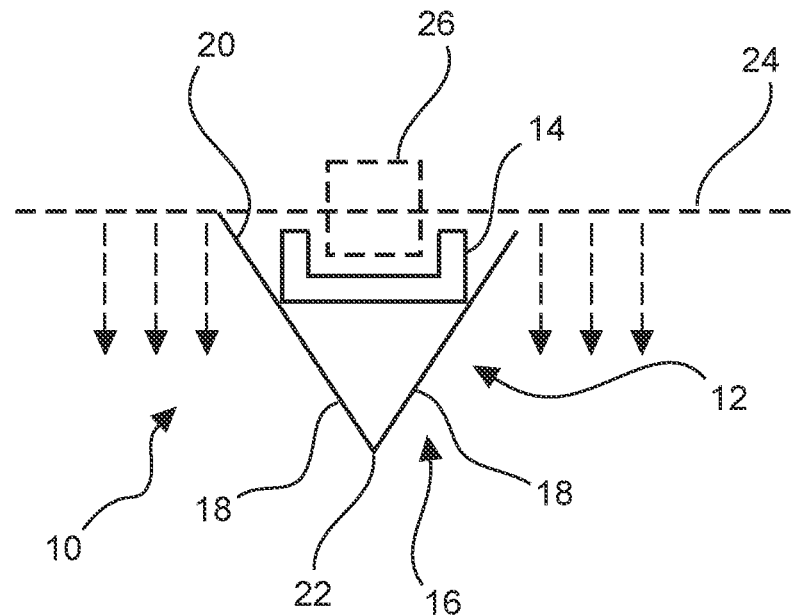
FIGS. 1*a* and 1*b* illustrate an example of a rail cover.

FIG. 1*a* shows an aerodynamic rail cover 10 for an operating room with laminar airflow. The rail cover 10 comprises at least one cover component 12. The cover component 12 comprises a base element 14 and an air guiding surface element 16 connected to the base element 14. The base element 14 is configured to be attached to a portion of a support rail of a ceiling mounted support arrangement of a medical imaging system. The air guiding surface element 16 forms an air guide to be mounted at least temporarily to cover a portion of the support rail and comprises two surface parts 18 that are extending from starting edges 20 on opposite sides of the base element to a common trailing edge. The rail cover component is configured to be movably attached to the support rail of the ceiling mounted support arrangement of a medical imaging system.

The rail cover component is configured to be movably connected to the support rail to be movable along the support rail.

In an option, the base element 14 and the air guiding surface element 16 are provided in an integrated manner. The surface element is thus merged with the cover component 12.

The laminar airflow may be provided as a laminar downflow, e.g. a laminar flow from above an operating table in a downward oriented manner, for example in a vertical direction.

It is noted that the examples show one rail cover component. However, in further example, two or more cover components are provided, e.g. to cover portions of a pair of rails.

Figure 1B:
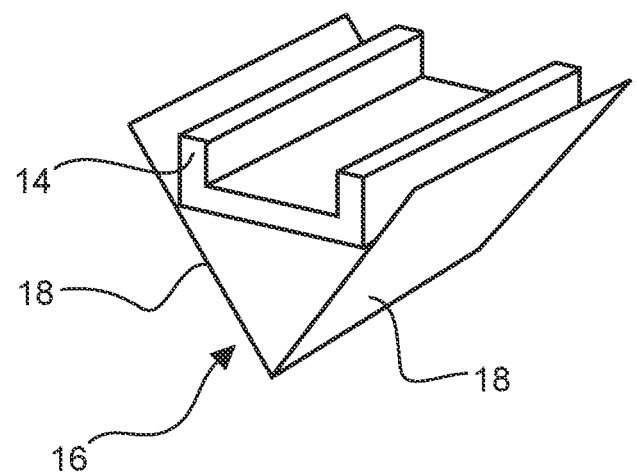
Figure 2:
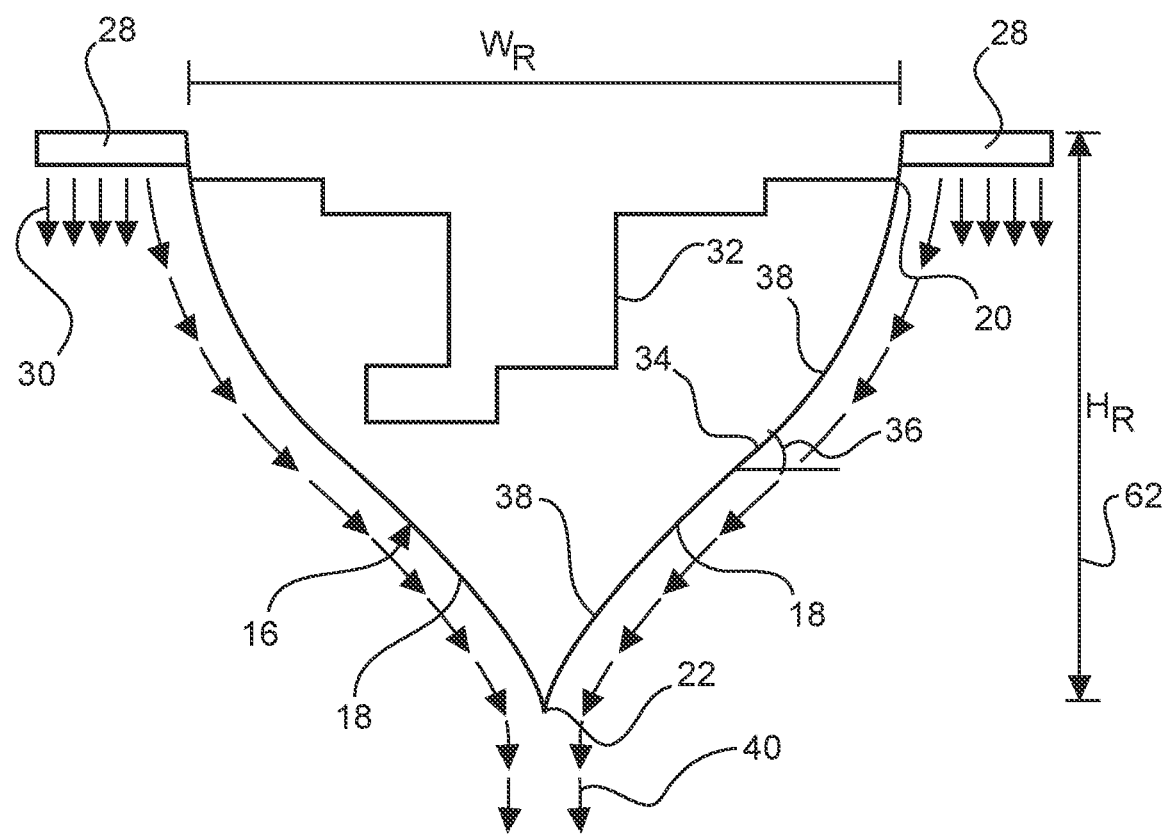
FIG. 2 illustrates a cross section of an example of a rail cover.

In FIG. 1*a*, FIG. 1B and FIG. 2 a single rail cover component is shown for explaining details of the rail cover segment per se.

Figure 3:
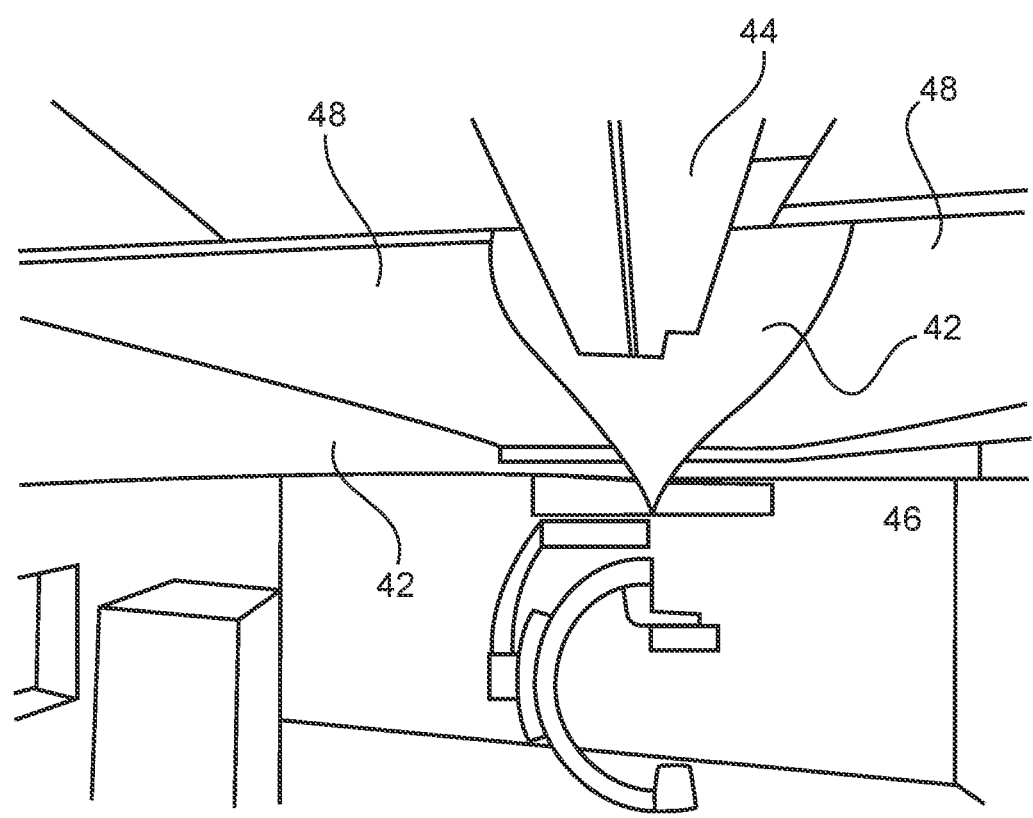
FIG. 3 shows a perspective view of an example of a rail cover segment attached to a support rail in an operating room.

FIG. 3 shows an example with a pair of support rails in the ceiling region, from which two support rails only one is further highlighted. The second support rail runs parallel to the first one.

Figure 4:
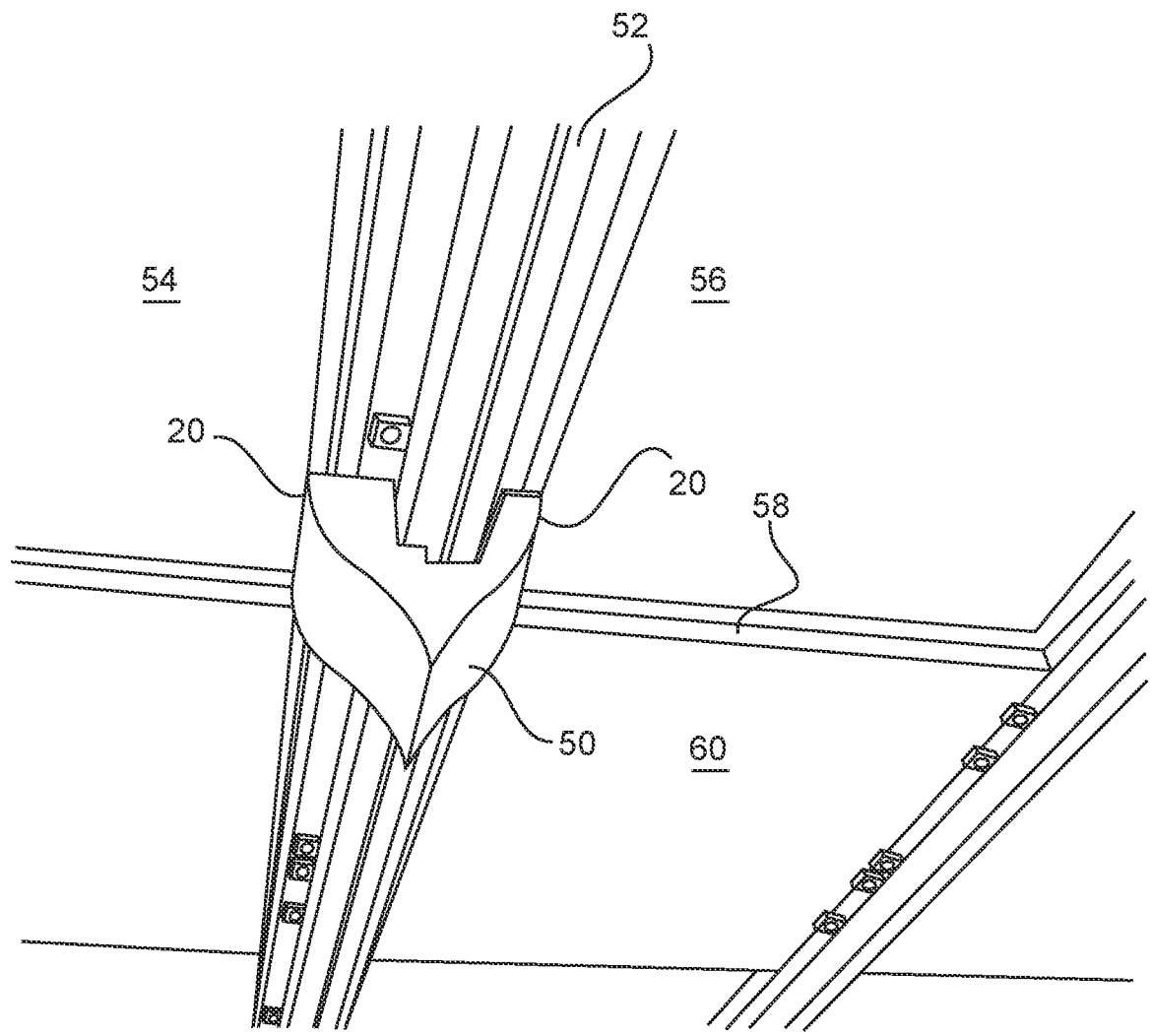
FIG. 4 shows a further perspective view of an example of a rail cover segment in a border region of a laminar airflow plenum.

FIG. 4 similarly shows a pair of support rails, of which one is further highlighted and referred to.

In an option, instead of a pair of rail, only one rail is provided.

Figure 7:
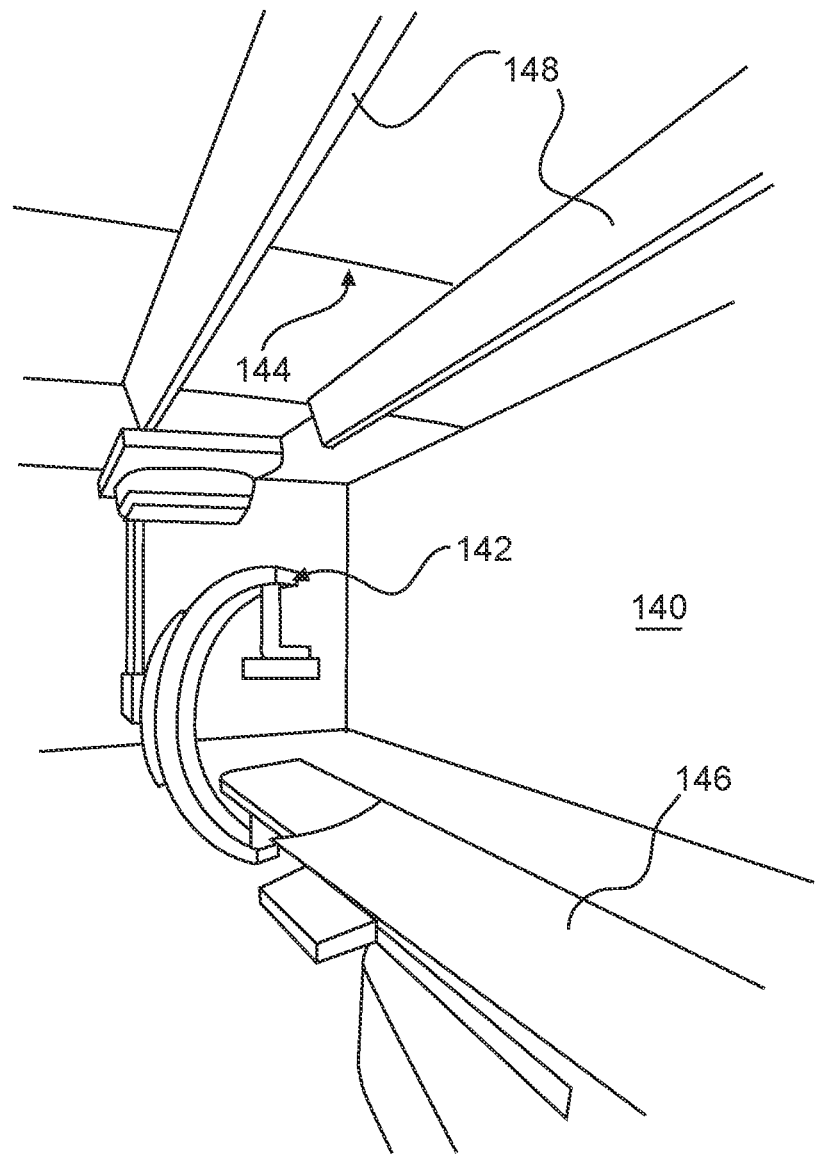
FIG. 7 schematically shows a perspective view of an operating room with a medical imaging system and laminar airflow system.

In a further option, two or more rail cover segments are provided along a single support rail, or on one of two support rails, or on both support rails FIG. 7 also shows an example with a pair of support rails above the patient table.

In another example, the laminar flow is provided in a horizontal direction or in an inclined direction relative to the vertical or horizontal direction.

In an example, the support rail interrupts, i.e. blocks, a laminar airflow field and thus forms the two adjacent laminar airflows.

In an example, the two surface parts are configured to bring together two adjacent laminar airflows in a streaming direction from the starting edges along the surface parts to the common trailing edge.

In an example, the two surface parts are configured to bring together two adjacent laminar airflows separated by the support rail to form a re-established, i.e. re-joined or joined, laminar airflow. The re-established laminar airflow thus provides an airflow recovery, or common air generation by combining two adjacent laminar airflows that otherwise would be separated by a turbulence zone.

In an example, the two surface parts are forming a wedge-like air guide.

The rail cover may comprise one cover component, e.g. when only one rail is arranged in a field where laminar airflow is provided.

The rail cover may comprise two cover components as a cover pair, e.g. when a pair of two rails is arranged in a field where laminar airflow is provided.

In an example, two cover components are provided for covering portions of each rail of a pair of support rails.

The rail cover may comprise more than two cover components, e.g. when more rails are arranged in a field where laminar airflow is provided and these rails need to be covered.

The ARC has an aerodynamic shape, which facilitates undisturbed passage of air, while also bringing the air flowing in through separate plenums together, thus creating an environment of uniform downward laminar airflow. In this sense, the ARC serves as an airflow stabilizer allowing a gradual and undisturbed transition of the air from laminar airflow (LAF) plenums to the region below the guiding rails, where the laminar flow is recovered. The ARC must have an aerodynamic shape, and in an example, it is resembling a droplet with a sharp trailing edge, in order to facilitate airflow recovery. In the examples, sides of the ARC are aligned flush with the edges of laminar airflow plenums to avoid any additional air pressure differences. Similar length of the sides of the ARC ensure that no pressure differences occur when two airflows meet at the end of the trailing edge.

In another example, the aerodynamic rail cover is provided as a bridging cover to be arranged in a separating region between two fields with laminar airflow. The aerodynamic rail cover thus bridges the laminar-flow-free zone. A rail can be provided in that zone.

The air guiding surface element is configured as an aerodynamic surface that can guide an airflow or air stream. The air guiding surface element is designed such that turbulences are prevented. The flow should remain laminar.

The re-establishing of a laminar airflow, i.e. the fixing of a gap or separation in a common laminar airflow supports the forming of an outer boundary layer of the laminar airflow, which outer boundary layer provides a separation between the controlled laminar airflow and the surrounding air in the operating room. Thus, hygienic conditions in the operating region are further improved.

The provision of the aerodynamic rail cover thus avoids influx of air from outside the downflow area.

The provision of the aerodynamic rail cover further also supports in restoring the laminar flow in the patient's zone which means additional comfort for staff and the patient.

The rail cover solution is a simple, cost effective solution that operates fully transparent for the user, i.e. it does not impose restrictions to ceiling mounted equipment, nor does it require attention from hospital staff to operate.

To cover at least some portions of a ceiling mounted rail system in a hybrid operating room environment, provides improved air supply. In a hybrid operating room (hybrid OR), the operating room is installed with such a ceiling mounted interventional X-ray system, resulting in a "hybrid OR". The ceiling mounted X-ray system may be suspended by a rail to move it along its longitudinal axis: This rail is generally placed directly above the patient and therefore crosses the laminar airflow plenum.

In FIG. 1a, a ceiling line 24 is shown indicating a ceiling for example in an operating room. Further, a rail structure 26 is basically indicated. FIG. 1b illustrates the example of FIG. 1a in a perspective view.

FIG. 2 illustrates a cross section of a further example of the rail cover. Boxes 28 indicate outlets of an air supply system that provides a field of laminar airflow, as indicated with arrows 30. Further, an outline 32 indicates a rail segment arranged between the two fields of laminar airflow. The air guiding surface element 16 is provided with the two surface parts 18 to cover the rail segment. The two surface parts 18 in their starting portions start at the starting edges 20, for example with the surface parts having a direction essentially perpendicular to a ceiling plane. The two surface parts, in their trailing edge portions, merge with an acute angle. In a still further option, additionally or alternatively, the two surface parts, in their middle portions, run in an angle wider than the acute angle at the trailing edge, but also narrower that at the starting edges.

In the trailing edge 22, the two surface parts meet and form a pointing edge with the two end portions of the surface parts having a small angle in relation to each other. In a middle section 34, the surface parts are arranged with a wider angle relative to each other, and also a wider angle 36 in relation to the ceiling plane. The middle portion can also be referred to as tangent line. In transition areas 38, the linear shape segment changes to a tangent line that gradually changes the direction.

In an example, the two surface parts, in their middle portions, run in an angle in a range of 30° to 60° in relation to the plane of the ceiling surface. For example, the middle portion run in an angle in a range of 40° to 50°, e.g. 45° in relation to the ceiling plane. In an example, the middle portions form an angle in relation to each other of around 90°.

The term "essentially" refers to a deviation in a range of, for example, up to +/−10° or up to +/−5°.

The acute angle of the trailing edge portions can also be referred to as pointed angle. The trailing edge portions thus form a smaller angle in relation to each other than the middle portion.

In an example, the surface parts are provided with transition portions between the starting portions and the middle portions as well as between the middle portions and the trailing edge portions. The transition portions, also referred to as transition zones, provide a smooth transition for the changes in the orientation of the surface. This supports in guiding and forming, i.e. creating a laminar airflow and to recover the laminar flow, i.e. to recombine two adjacent laminar air flow streams.

Adjacent layers of the laminar airflow are thus gradually guided along the surface parts leading to a repaired or recombined laminar airstream, as indicated with arrows 40.

FIG. 3 shows a perspective view of an example 42 of the rail cover segment attached to a support rail 44 in an operating room. An imaging system such as an X-ray C-arm system 46 is shown in the background. Plenums 48 of laminar air flow are arranged on both sides of the rail 44. The plenums represent air outlets for achieving the laminar airflow.

FIG. 4 shows a further perspective view of an example of a rail cover segment 50 in a border region of a laminar airflow plenum. A rail 52 is indicated that serves as support rail for an imaging system (not further shown). A laminar airflow source is arranged in the ceiling area. Due to the arrangement of the rail 52 (or another obstacle arranged in a similar manner, the laminar airflow field is provided in form of a first laminar airflow plenum 54 on one side of the rail 52 and a second laminar airflow plenum 56 on the other side of the rail 52. A border region 58 is provided as an edge of the laminar airflow field. On the other side of the border region, a field 60 without laminar airflow is provided.

The starting edges 20 are arranged next to border regions of the first and second laminar airflow plenum, for example flush, i.e. face-to-face, such that a region between two laminar airflow fields blocked by the rail, i.e. an intermediate region, which blocked region does not provide a laminar airflow in a plane of the laminar airflow plenum field, is bridged by the air guiding surface element to provide a re-established laminar airflow of the two laminar airflow fields downstream, i.e. below, the trailing edge.

Thus, a laminar airflow is provided below the aerodynamic rail cover to improve the effect of the laminar airflow in form of providing clean or controlled air to a patient, and not contaminated air from the surrounding air.

In an example, the starting edges are configured to be positioned flush with the border regions of the laminar airflow plenum. For example, the starting edges are face-to-face, e.g. aligned with the border regions of the laminar airflow plenum. As an example, the starting edges form virtually the same surface.

The term "laminar airflow plenum" relates to a plane in which airflow outlets are arranged to generate the laminar airflow downstream of the plenum.

The blocked regions may be caused by support rails of a ceiling mounted support arrangement of a medical imaging system. In an example, the rails are mounted below a ceiling, while the air outlets are arranged in a ceiling plane, or at least in a suspended ceiling covering. The rails are mounted below in order to be able to provide a slidable guiding of equipment of an imaging system along the rails.

If the laminar airflow is generated by outlets in a wall plane and not in a ceiling plane, and the rail is arranged in front of the wall plane, a respectively aligned orientation of the aerodynamic rail cover is provided.

In the ceiling arrangement, the aerodynamic rail cover is provided to the rail from below, while the airflow is oriented in a downward direction, such as in the vertical direction.

In an example, not further shown, the two surface parts each provide an essentially equal guiding length between the starting edges and the trailing edge.

The term "essentially equal" length refers to a substantially equal length. The term "essentially equal" length relates to a deviation in length of up to +/−20%, e.g. up to +/−10%, or up to +/−5%. The provision of an essentially equal length ensures that air traveling (or streaming) along the surfaces on both sides is re-established, i.e. re-joined at the trailing edge with the same air speed, or at least nearly the same air speed. Thus, underpressure regions are provided that could otherwise lead to drawing in contaminated air from outside the laminar airflow.

In an example, the surface parts are arranged symmetrical, and the trailing edge forms a virtual symmetry axis.

In a further example, shown as option in FIG. 2, the cover component has a downward protruding dimension 62 of maximum 50 cm, for example, 21 cm. Depending on the geometry of the X-ray system, the value can differ.

The term "downward protruding dimension" relates to a direction from the starting edges towards the trailing edge, e.g. perpendicular to a ceiling surface.

The maximum height is provided for preventing collisions with ceiling suspended systems such as operating room (OR-) light booms and the like.

The term "approximately" refers to a deviation of max. +/−15%, such as +/−10% or +/−5%, In a still further example, a width $W_R$ of the rail cover segment is defined by a distance between the starting edges, and a height $H_R$ of the rail cover segment is defined by a distance from a plane formed by the starting edges to the common trailing edge. The width $W_R$ is equal or larger than the height $H_R$.

In an example, a ratio of width to height is 1:1. In another example, the ratio is larger than one, i.e. the height is smaller than the width. In another example, the ratio is smaller than one, i.e. the height is larger than the width.

In an option, the rail cover component is configured to be slidably attached to the support rail of the ceiling mounted support arrangement of a medical imaging system.

In an example, the base element is configured to be slidably attached to the support rail.

The sliding may be provided by some roller bearings or guiding elements to be moved along the rail. In another example, the base element is configured to be temporarily attached to the support rail of the ceiling mounted support arrangement of a medical imaging system in a fixed manner.

For example, the movable aerodynamic rail cover sort of repairs disturbances of a laminar down flow in hybrid operating rooms by ceiling mounted X-ray systems.

It must be noted that although the rails partly block the downflow, which per se would cause disturbances which in turn may result in mixing of clean and dirty air and as such can compromise air cleanliness, the cover solves this. The rail without rail cover can cause a low-pressure area directly under the rails, which can suck in air from outside the laminar area, thus mixing clean and "dirty air. However, the rail-cover covers the rail with an aerodynamic shape and prevents the occurrence of a low-pressure and consequential mixing of clean and dirty air. The rail cover is movable along the longitudinal axis so that the X-ray system can still pass.

In an example, a ceiling mounted X-ray system is suspended on a rail to move it along its longitudinal axis: This rail is placed directly above the patient and therefore crosses the laminar airflow plenum. The rail is covered by an aerodynamic cover where it crosses the LAF-plenum, to enable undisturbed laminar downflow. At the same time, the X-ray systems carriage should also be allowed to travel along the full length of the ceiling rail, so that the rail cover needs to be movable.

Figure 5:
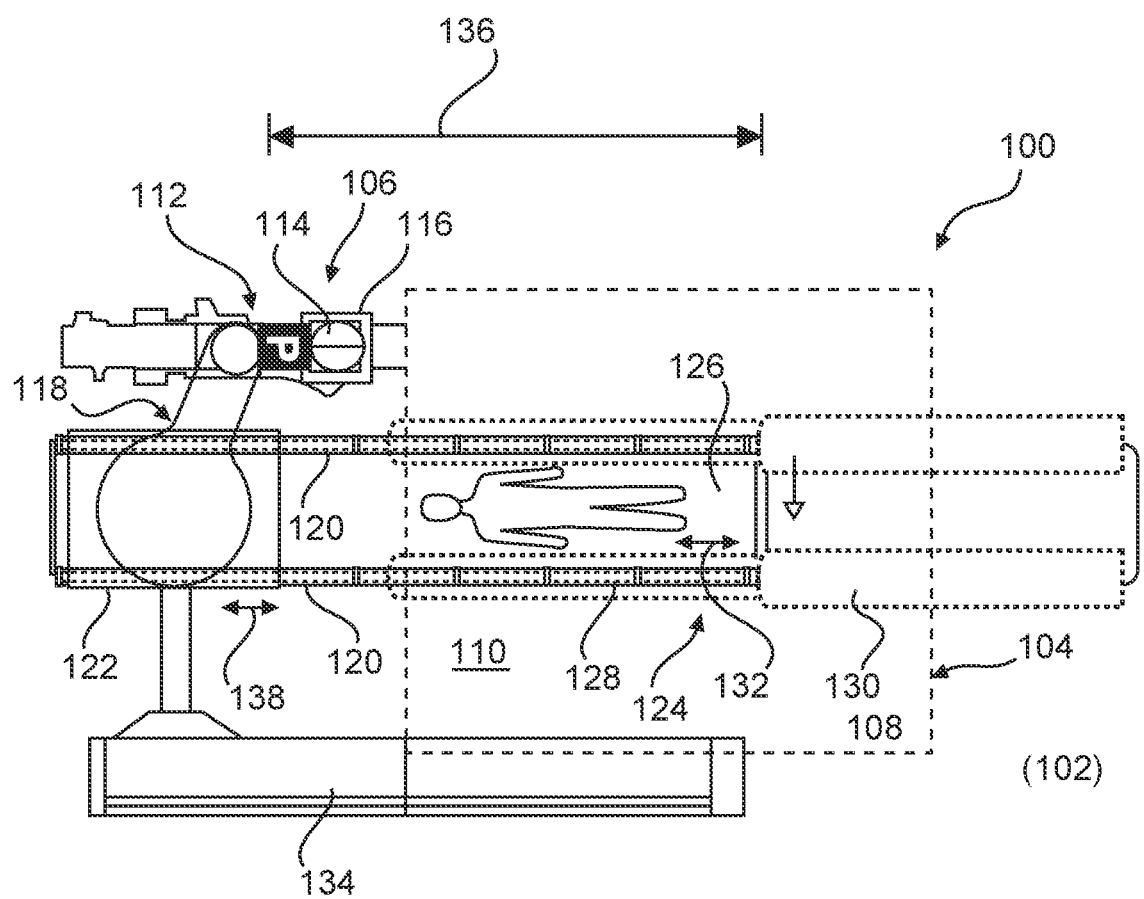
FIG. 5 schematically shows a top view of an operating room arrangement with a laminar airflow system and a medical imaging system. A rail arrangement is provided that is equipped with aerodynamic rail covers.

FIG. 5 schematically shows a top view of an operating room arrangement 100 with a laminar airflow. The operating room arrangement 100 comprises at least a ceiling region 102, not further shown. The operating room arrangement further comprises a laminar airflow system 104, also not further shown and a medical imaging system 106.

The laminar airflow system 104 comprises at least one laminar airflow outlet 108 configured to provide at least one laminar airflow plenum 110.

The medical imaging system 106 comprises an image acquisition arrangement 112 with a source 114 and a detector 116. For example, the image acquisition arrangement may be provided as an X-ray imaging apparatus. Further, the medical imaging system 106 comprises a support arrangement 118 with at least one support rail 120 mounted in the ceiling region and a carriage 122 that is movable along at least a part of the support rail 120. At least one of the source and detector is movably supported by the carriage. At least a part of the at least one support rail is arranged downstream the laminar airflow outlet. At least one rail cover 124 for covering at least one part of the support rail is provided. The rail cover is provided as an aerodynamic rail cover according to one of the examples above.

The at least one laminar airflow outlet is configured to provide an airflow towards a patient table 126.

In an example, as indicated in FIG. 5, two cover segments 128, 130 are provided for each rail. One of the two cover segments is fixedly mounted to the support rail to provide a fixed rail cover segment, and the other of the two cover segments is arranged on the rail in a displaceable manner. For example, the cover segment can temporarily be moved away and moved back in place later. In other words, an adjustable rail cover segment is provided. In FIG. 5, the cover segment 128 is movable, as indicated with arrow 132. The cover segment 130 is fixed. For example, the adjustable rail cover segment is provided as a movable cover segment. The movable cover segment 128 is at least partly insertable into the fixed rail cover segment 130, as indicated in FIGS. 6a and 6b. In another option, the fixed rail cover segment is at least partly insertable into the movable cover segment. The two cover segments are forming a telescopic cover component.

In FIG. 5, also further equipment such as a ceiling suspended display (not shown in detail) and an interface arrangement 134 is indicated.

In FIG. 5, an arrow 136 indicates a longitudinal range in which the carriage 122 can be moved along the rails 120. An arrow 138 indicates the movability of the carriage 122 along the rails 120.

The movable cover segment 128 can be referred to as movable ARC, the fixed cover segment 130 can be referred to as fixed ARC docks.

FIGS. 6a and 6b show a rail arrangement with rail covers resulting in an adaptable field of laminar airflow. FIG. 6a shows a carriage for an X-ray imaging system in a first position, and FIG. 6b shows the carriage in a second position with displaced cover segments.

In another example, not further shown in detail, the rail cover component is an adaptable rail cover component comprising at least one telescopic cover segment with a plurality of telescopic cover elements. In addition, or alternatively, the rail cover component is an adaptable rail cover component comprising at least one bellows cover segment.

As a variation, also not shown in detail, one end of the adaptable cover component is configured to be fixed, whereas the other end is configured to be displaceable providing a rail cover component with adaptable length.

In still another example for a moveable rail cover, the cover is a harmonic folding rail cover. In this embodiment, the ARC length can be varied by compression or expansion of a flexible bag (like a bellow) which covers the rail. The outer contour of the folding ARC is similar shaped as described above and below, but consists of small segments which can fold against each other (compressed) or unfolded (expanded).

In an example, not further illustrated, a laminar airflow system for an operating room with a medical imaging system is provided. The airflow system comprises at least one laminar airflow outlet configured to provide at least one laminar airflow plenum. The at least one laminar airflow outlet is configured to provide an airflow towards a patient table. A support rail of a ceiling mounted support arrangement of a medical imaging system can be arranged downstream the laminar airflow outlet or adjacent to the laminar airflow plenum. At least one rail cover for covering at least one part of the support rail is provided, which rail cover is provided as an aerodynamic rail cover according to one of the above and below described examples.

The term "laminar airflow plenum" refers to an area within the operating room where laminar airflow is provided from the ceiling down onto a predefined area plenum of operation. The laminar airflow is preferably providing a flow of clean air, e.g. sterile air. This helps in minimizing the risk of infection of the patient due to contaminated air from the e.g. surrounding.

In another example, provided in addition or alternatively, also not further illustrated, a medical imaging system for an operating room with laminar airflow is provided. The imaging system comprises an image acquisition arrangement with a source and a detector. The imaging system further comprises a ceiling mounted support arrangement with at least one support rail and a carriage movable along at least a part of the support rail. The imaging system further comprises at least one rail cover for covering at least one part of the support rail. At least one of the source and detector is movably supported by the carriage. At least a part of the at least one support rail can be arranged downstream a laminar airflow outlet or adjacent to a laminar airflow plenum provided by the laminar airflow outlet. The rail cover is provided as an aerodynamic rail cover according to one of the above and below described examples.

FIG. 7 schematically shows a perspective view of an operating room 140 with a medical imaging system 142 and laminar airflow system 144. Rails (covered by the aerodynamic rail cover) are arranged in ceiling plane. A patient table 146 is provided, together with further imaging or examination equipment. The aerodynamic rail covers, indicated with reference number 148, result in that a continuous field of laminar airflow is provided in the level of the patient table due to the recombining of the two adjacent fields of laminar downflow.

Figure 8:
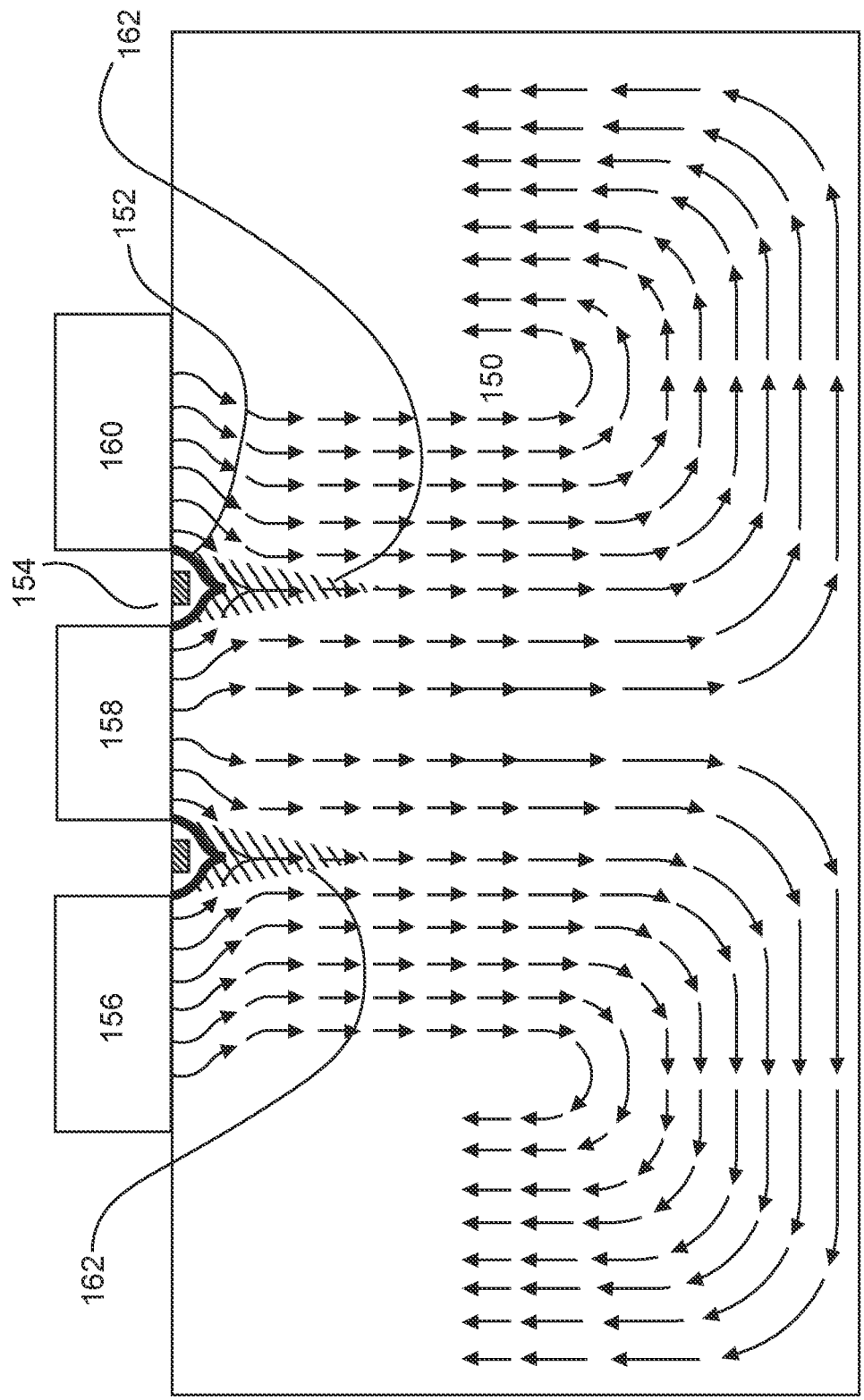
FIG. 8 illustrates a vertical cross section of a flow field simulation with two rail covers arranged in parts with ceiling mounted rails.

FIG. 8 illustrates a vertical cross section of a flow field simulation 150 with two rail covers 152 arranged in parts with ceiling mounted rails 154. Three boxes 156, 158, 160 for generating a laminar airflow field below are arranged. The area below the boxes is separated by the two rails 154. However, by providing the two rail covers 152 as aerodynamic rail covers, re-established laminar airflow 162 below the rails is provided. As can also be seen from the simulation, the laminar downflow provides an area for the operating table which area can be supplied with pre-treated or pre-conditioned. Surrounding air does not enter the laminar flow field. In the blocked areas, where the rails are provided, the aerodynamic rail covers result in the re-established laminar air flow.

Figure 9:
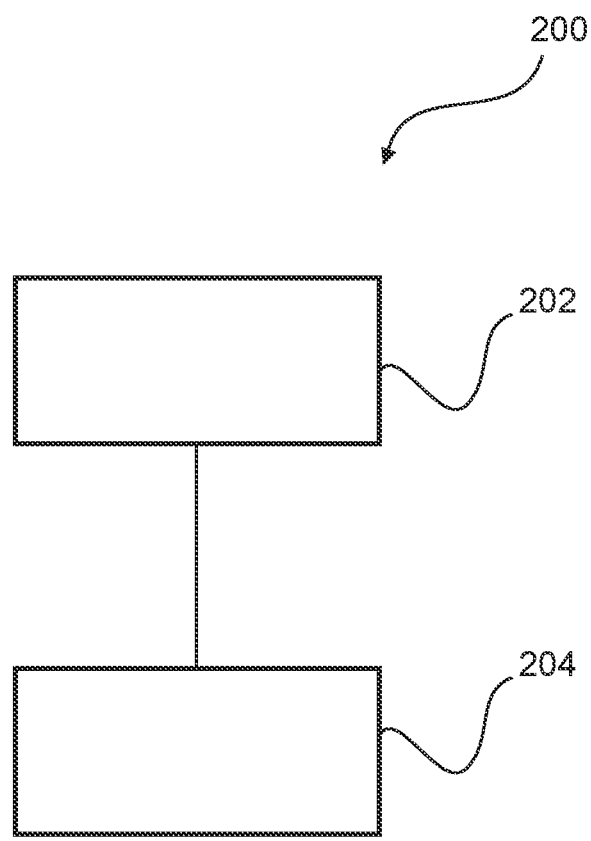
FIG. 9 shows basic steps of an example of a method for providing a laminar airflow for an operating room.

FIG. 9 shows a method 200 for providing a laminar airflow for an operating room. The method comprises the following steps:

In a first step 202, also referred to as step a), a first plenum of laminar airflow and a second plenum of laminar airflow are provided. The first and second plenum are separated from each other by a laminar-flow-free region, or are at least disturbed in an area between the first and second plenum.

In a second step 204, also referred to as step b), a border portion of the first laminar airflow is guided along a first surface part of an air guiding surface, and a border portion of the second laminar airflow is guided along a second surface part of the air guiding surface, wherein the first and second surface parts are extending from starting edges close to the first and second plenum, respectively, to a common trailing edge, wherein the first surface part and the second surface part and the training edge are forming an air guide covering a portion of the laminar-flow-free region. The rail cover component is configured to be movably attached to the support rail of the ceiling mounted support arrangement of a medical imaging system.

Figure 10:
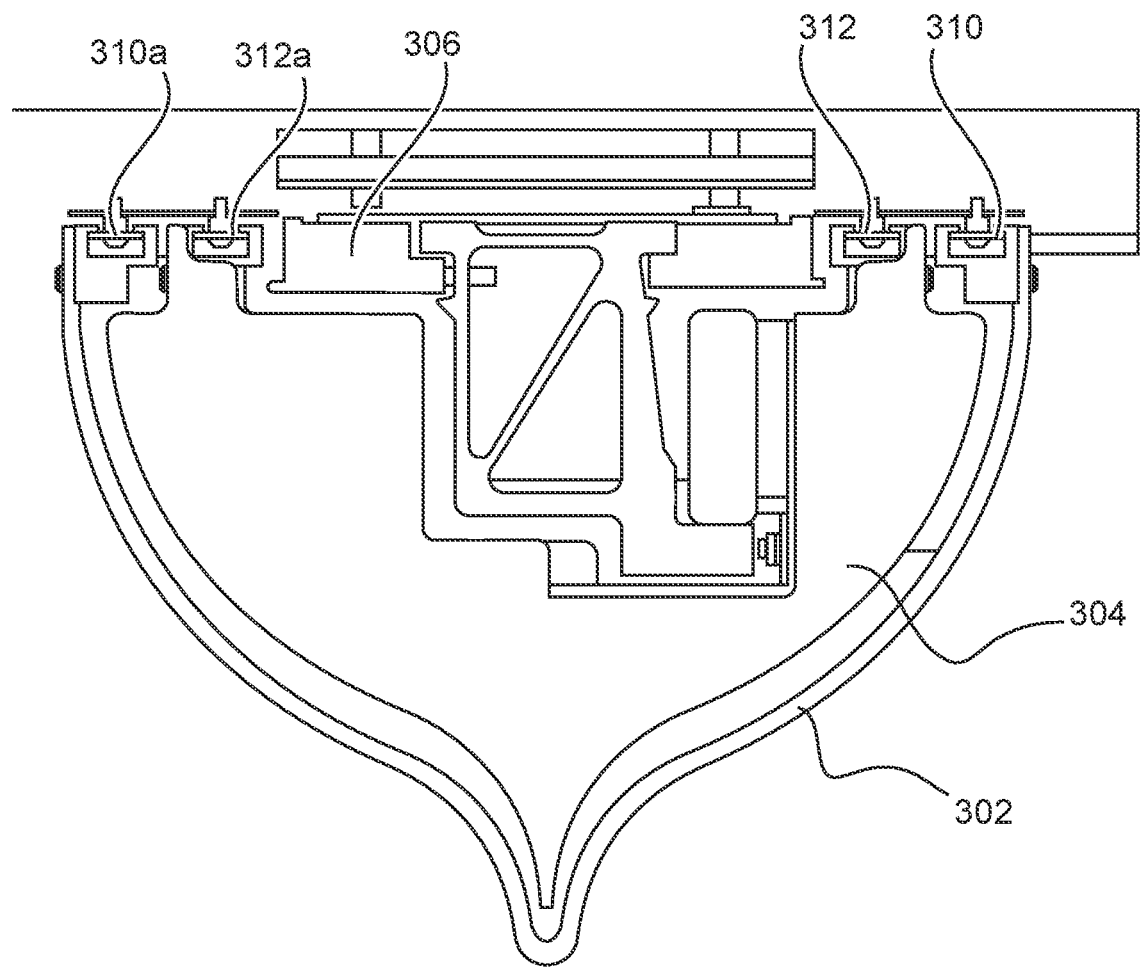
FIG. 10 shows a cross section of an example with a sliding guiderail arrangement for cover support.

FIG. 10 shows a cross section of an example with a sliding guiderail arrangement for cover support. A first cover segment 302 is provided with a larger cross section such that in can be moved over a second cover segment 304. Further, a ceiling support rail 306 of an imaging system is indicated. A sliding guiderail arrangement 308 is provided with cover support guiderails to be arranged along each longitudinal side of the support rail 306. A first cover support guiderail 310 is provided for the first cover segment 302 and a second cover support guiderail 312 is provided for the second cover segment 304. A further first and second cover support guiderails 310a, 312a are provided on the other side. The rail cover component is thus slidably suspending from the cover support guiderails.

Figure 11:
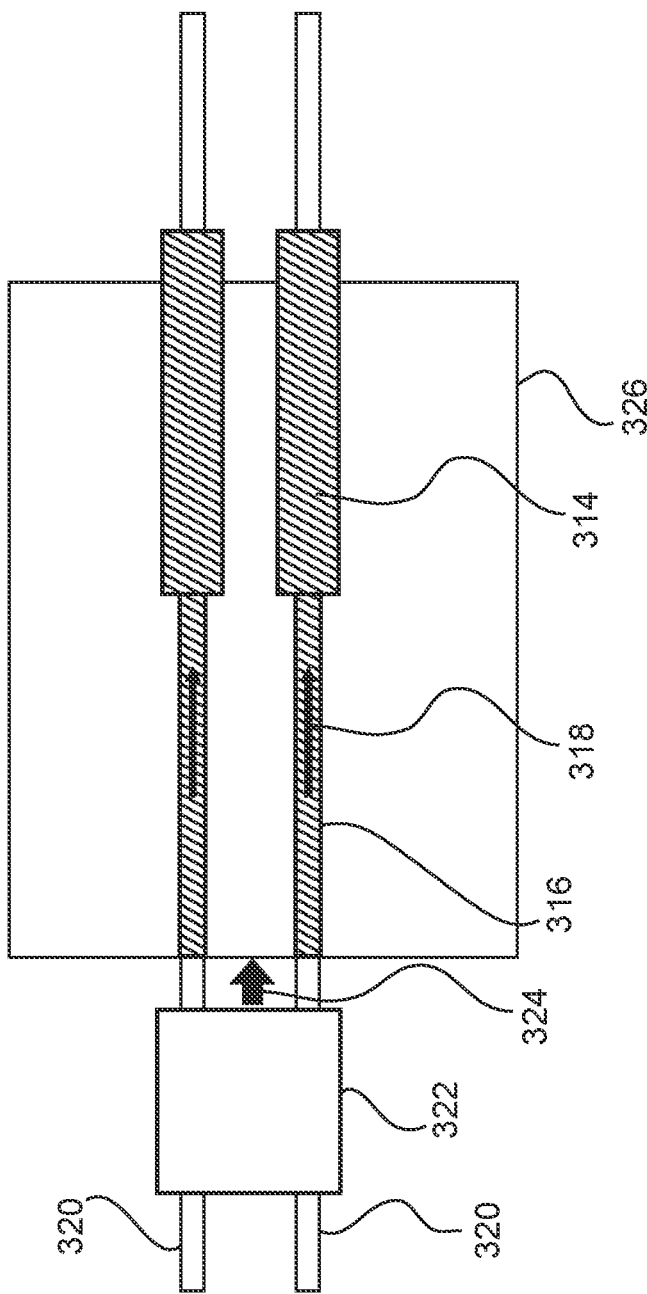
FIG. 11 shows a bottom view of a ceiling support rail of an imaging system with a carriage and two cover segments on each support rail.

FIG. 11 shows a bottom view of a ceiling support rail of an imaging system with a carriage and two cover segments on each support rail.

Two cover segments are provided. A first cover segment 314 is provided with a larger cross-section and a second cover segment 316 is provided with a smaller cross-section and can be moved into or below the first cover segment. At least one cover segment is arrangeable on the rail in a temporarily displaceable manner to provide an adjustable rail cover segment. One cover segment is at least partly insertable into the other cover segment;

A pair of support rails 320 is provided, on which a carriage 322 is moved along, as indicated with first moving arrows 324. A laminar air flow field 326 from the ceiling region is also indicated. When the carriage 322 is moved towards the laminar air flow field 326, the second cover segments 316 are pushed to the side, as indicated with pushing arrow 328. The first cover segment 314 and the second cover segment 316 have approximately equal length.

Figure 12:
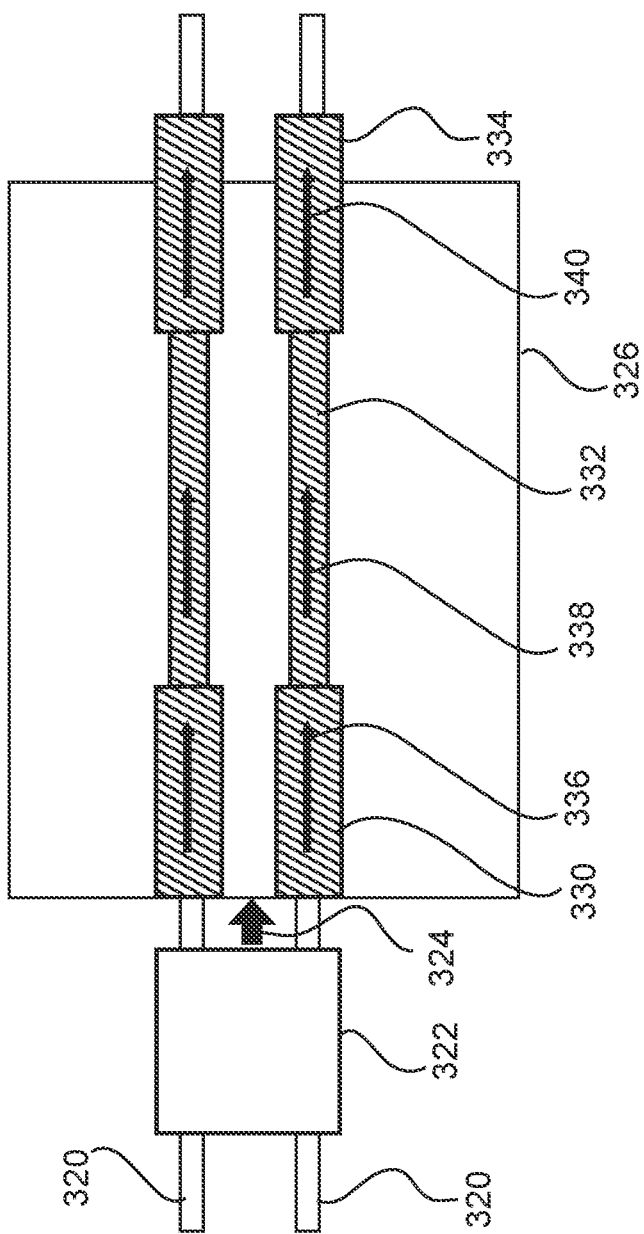
FIG. 12 shows a bottom view of a ceiling support rail of an imaging system with a carriage and three cover segments on each support rail.

In an example, also indicated in FIGS. 11 and 12, the support rail 320 reaches across the outer boundaries of the laminar airflow outlet, i.e. the boundaries of the laminar air flow field 326. The aerodynamic rail cover comprises at least two segments from which at least one is provided as an outer movable segment. Further, the at least one outer movable segment is arrangeable in an area of the outer boundaries of the laminar airflow outlet.

FIG. 12 shows a further example of a ceiling support rail of an imaging system with a carriage and three cover segments on each support rail, also in a bottom view.

Three cover segments are provided: a first outer segment 330, a middle segment 332, or inner segment, and a second outer segment 334. At least one of the two outer segments 330, 334 is provided as an outer movable segment. In an option, shown in FIG. 12, both of the two outer segments 330, 334 are provided as outer movable segments. In an option, not shown, only one of the two outer segments is provided as an outer movable segment and the other one of the two outer segments is provided as an outer static segment.

In a further option, also shown in FIG. 12, the middle segment is provided as a middle movable segment. In an option, not shown, the middle segment is provided as a middle static segment.

In an option, two or more middle segments are provided.

In an example, the segment closest to the carriage and the middle segment (or section) is movable, but the segment most distal from the carriage may remain fixed (similar to a two-segment configuration indicated in FIG. 11.

The two outer segments are provided with a wider cross-section such that they can be moved into each other. For example, at least one outer movable segment can be moved over the middle segment. Or the middle segment can be moved into the outer segment. Or they can both be moved in relation to each other.

In case the outer segment is an outer static segment, the middle segment is a middle movable segment that can be moved below the outer static segment.

In case the middle segment is a middle static segment, the outer segment is an outer movable segment that can be moved over the outer static segment.

When the carriage 322 is moved towards the laminar air flow field 326, the first outer segment 330 is pushed to the side and over the middle segment, as indicated with pushing arrow 336. When pushed even further, the middle segment 332 is also pushed 338 into the second outer segment 334. Still further, also the second outer segment 334 can be pushed 340. The outer segments have approximately half the length of the middle segment. It is noted that the second outer segment 334 can be designed to remain static, depending on the required travel length of the carriage.

Figure 13:
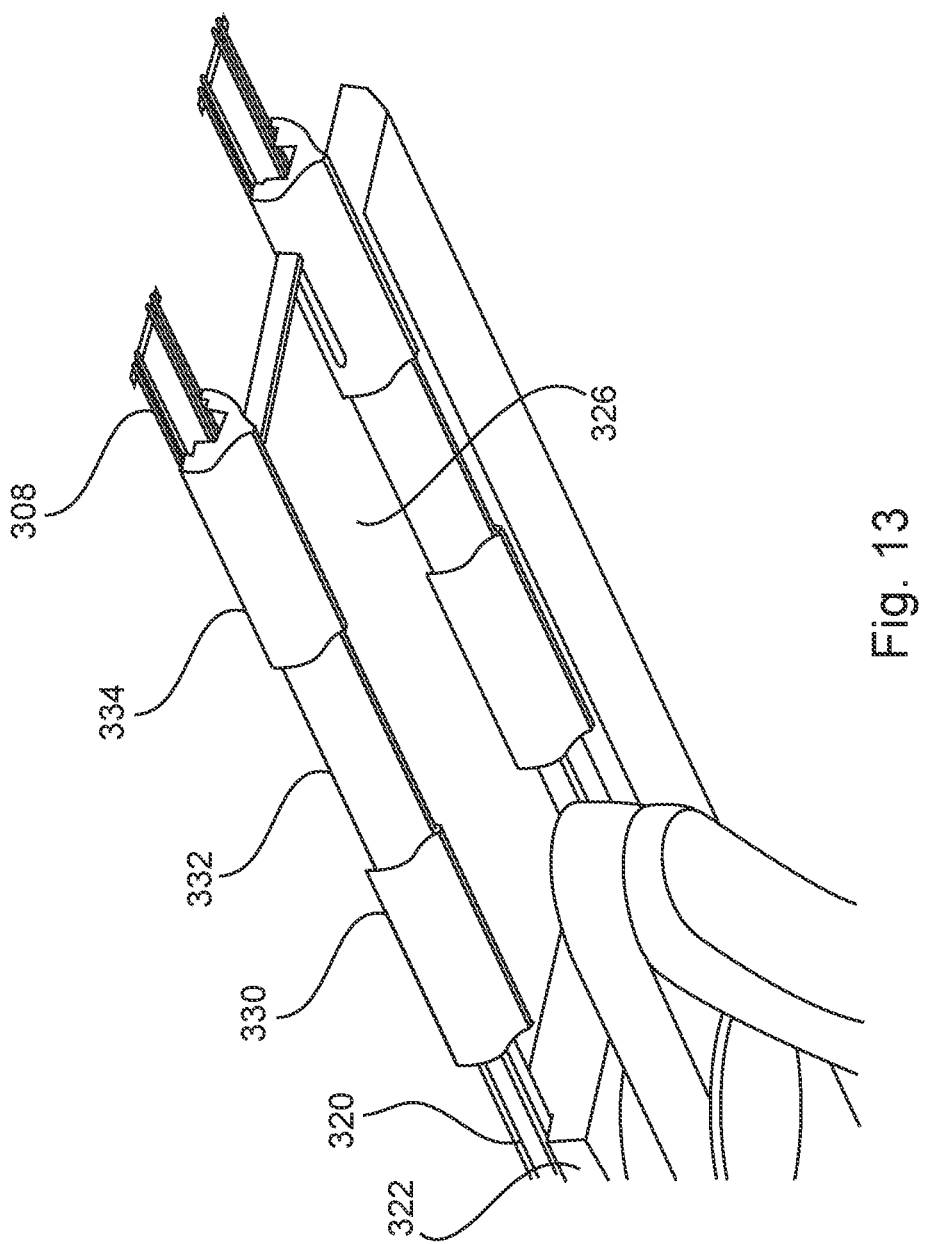
FIG. 13 shows a perspective view of the example of FIG. 12.

FIG. 13 shows a perspective view of the example of FIG. 12. In addition to the cover segments, also the sliding guiderail arrangement 308 is indicated.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An aerodynamic rail cover for an operating room with laminar airflow, the aerodynamic rail cover comprising:
   a cover component comprising:
      a base element configured to be attached to a portion of a support rail of a ceiling mounted support arrangement of a medical imaging system, wherein the base element attaches to the portion of the support rail such that the cover component is movable along the support rail; and
      an air guiding surface element connected to the base element, the air guiding surface element forming an air guide configured to be mounted at least temporarily to cover a portion of the support rail, the air guiding surface element comprising two surface parts that extend from starting edges on opposite sides of the base element to a common trailing edge.

2. The aerodynamic rail cover according to claim 1, wherein the cover component is configured to be slidably attached to the support rail.

3. The aerodynamic rail cover according to claim 2, further comprising a sliding guiderail arrangement with cover support guiderails to be arranged along each longitudinal side of the support rail; and
   wherein the cover component is slidably suspended from the cover support guiderails.

4. The aerodynamic rail cover according to claim 1, further comprising at least two cover segments;
   wherein at least one cover segment is arrangeable on the support rail in a temporarily displaceable manner to provide a first adjustable rail cover segment;
   wherein one cover segment is at least partly insertable into a second adjustable cover segment; and
   wherein the at least two cover segments form a telescopic cover component.

5. The aerodynamic rail cover according to claim 1, further comprising three cover segments that include a first outer segment, a middle segment, and a second outer segment; and
   wherein the first outer segment and the second outer segment have a wider cross-section than the middle segment, such that the first outer segment and the second outer segment are movable over the middle segment.

6. The aerodynamic rail cover according to claim 1, wherein the cover component comprises at least one bellows cover segment;
    wherein a first end of the cover component is configured to be fixed, and a second end of the rail cover is configured to be displaceable to provide the cover component with an adaptable length.

7. The aerodynamic rail cover according to claim 1, further comprising a magnetic coupling configured to connect the cover component to a carriage of an imaging system and the carriage is movable along the support rail,
    wherein the coupling is dis-connectable, if the carriage moves outside a covering range of the aerodynamic rail cover.

8. The aerodynamic rail cover according to claim 1, wherein the starting edges are configured to be arranged next to border regions of a laminar airflow plenum such that an intermediate region between two laminar airflow fields is bridged by the air guiding surface element in order to provide a re-established laminar airflow of the two laminar airflow fields downstream the common trailing edge.

9. The aerodynamic rail cover according to claim 1, wherein a width of a rail cover segment is defined by a distance between the starting edges, and a height of the rail cover segment is defined by a distance from a plane formed by the starting edges to the common trailing edge; and wherein the width is equal or larger than the height; and
    wherein each of the two surface parts at least one of:
        (i) in a starting portion, extend from the starting edges in a perpendicular direction to a plane of a ceiling surface;
        (ii) in a trailing edge portion, merge with an acute angle; or
        (iii) in middle portions, run in an angle wider than the acute angle at the common trailing edge, but also narrower than at the starting edges.

10. A laminar airflow system for an operating room with a medical imaging system, the airflow system comprising:
    at least one laminar airflow outlet configured to provide at least one laminar airflow plenum and provide an airflow towards a patient table;
    the support rail arrangeable downstream from the laminar airflow outlet or adjacent to the laminar airflow plenum; and
    the aerodynamic rail cover according to claim 1.

11. The laminar airflow system according to claim 10, wherein the support rail reaches across outer boundaries of the laminar airflow outlet; and
    wherein the aerodynamic rail cover comprises at least two segments from which at least one segment is provided as an outer movable segment;
    wherein the outer movable segment is arrangeable in an area of the outer boundaries of the laminar airflow outlet.

12. The laminar airflow system according to claim 11, wherein the aerodynamic rail cover comprises at least three segments, including the at least one outer movable segment and a middle segment; and
    wherein the at least one outer movable segment has a wider cross section than the middle segment such that the at least one outer movable segment and the middle segment are moveable into each other.

13. A medical imaging system for an operating room with laminar airflow, the imaging system comprising:
    an image acquisition arrangement with a source and a detector;
    a ceiling mounted support arrangement with a support rail and a carriage movable along at least a part of the support rail,
    wherein at least one of the source and detector is movably supported by the carriage,
    wherein at least a part of the support rail of the ceiling mounted support arrangement of the medical imaging system is arrangeable downstream a laminar airflow outlet or adjacent to a laminar airflow plenum provided by the laminar airflow outlet; and
    the aerodynamic rail cover according to claim 1.

14. An operating room arrangement with a laminar airflow, the arrangement comprising:
    a ceiling region;
    a laminar airflow system comprising at least one laminar airflow outlet configured to provide at least one laminar airflow plenum, the at least one laminar airflow outlet configured to provide an airflow towards a patient table;
    a medical imaging system comprising an image acquisition arrangement with a source and a detector and a support arrangement with at least one support rail mounted in the ceiling region and a carriage movable along at least a part of at least one support rail, wherein at least one of the source and detector is movably supported by the carriage and at least a part of the at least one support rail is arranged downstream of the at least one laminar airflow outlet; and
    the aerodynamic rail cover according to claim 1.

15. A method for providing a laminar airflow for an operating room, the method comprising:
    providing a first plenum of laminar airflow and a second plenum of laminar airflow; wherein, in a plane of generation, the first plenum and the second plenum are separated from each other by a laminar-flow-free region;
    movably attaching a cover component to a support rail of a ceiling mounted support arrangement of a medical imaging system, wherein the cover component comprises a base element and an air guiding surface element connected to the base element;
    guiding a border portion of the first plenum of laminar airflow along a first surface part of an air guiding surface of the air guiding surface element, and guiding a border portion of the second plenum of laminar airflow along a second surface part of the air guiding surface, wherein the first surface part and the second surface part are extending from starting edges positioned close to the first plenum of laminar airflow and the second plenum of laminar airflow, respectively, to a common trailing edge, wherein the first surface part and the second surface part and the trailing edge forms an air guide covering a portion of the laminar-flow-free region.

* * * * *